United States Patent [19]
Broedel et al.

[11] Patent Number: 5,910,509
[45] Date of Patent: Jun. 8, 1999

[54] ANTIMICROBIAL AGENT FOR AGRICULTURE

[76] Inventors: Sheldon E. Broedel, 4 Prestwick Sq., Baltimore, Md. 21228; Lawrence I. Kruse, 129 Broad St., P.O. Box 326, Claremont, N.H. 03743

[21] Appl. No.: 08/666,984

[22] Filed: Jun. 20, 1996

[51] Int. Cl.$^6$ ................................. A01N 43/16
[52] U.S. Cl. .................. 514/456; 514/291; 514/307; 514/309; 514/310; 514/432; 514/434; 514/454; 514/455
[58] Field of Search .................. 549/386, 399, 549/404, 405, 407, 409; 514/454, 455, 456

[56] References Cited

U.S. PATENT DOCUMENTS

| | | | |
|---|---|---|---|
| 2,053,095 | 9/1936 | Maximoff | 260/96 |
| 2,417,584 | 3/1947 | Birkinshaw et al. | 195/36 |
| 4,196,280 | 4/1980 | Umezawa et al. | 536/17 R |
| 4,255,564 | 3/1981 | Umezawa et al. | 536/17 R |
| 5,189,150 | 2/1993 | Zeeck et al. | 536/6.5 |
| 5,217,990 | 6/1993 | Hansske et al. | 514/450 |

FOREIGN PATENT DOCUMENTS

WO 9519706  7/1995  WIPO.

OTHER PUBLICATIONS

Itabashi et al., Chemical Abstracts, vol. 120, abstract 293681, 1993.

Hiroyuki Haraguchi et al., Chrysodin, An Antifungal Antimetabolite, Agric Biol. Chem., 54(8):2167–2168, 1990.

Ken Yasukawa et al., Azaphilones Inhibit Tumor Promotion by 12–O–Tetra–Decanoylphorbol–13–Acetate in Two–Stage Carcinogenesis in Mice, Oncology, 51:108–112, 1994.

Pieter S. Steyn et al., The Structure of Dihydrodeoxy–8–EPI–Austdiol and the Absolute Configuration of the Azaphilones, J.C.S. Perkin I, pp. 204–206, 1976.

J. Anke et al., Deflectins, New Antimicrobial Azaphilones from *Aspergillus Deflectus*, The Journal of Antibiotics, vol. XXXIV No. 8, pp. 923–928, Aug. 1981.

von Annemarie Closse et al., Isolierung Und Konstitutionsermittlung Von Chrysodin, Helvetica Chemica Acta, vol. 56, Fasc. 1, Nr. 276 (1973).

F.C. Chen, The Chemistry of Fungi. Part LXIV. The Structure of Monascin: The Relative Stereochemistry of the Azaphilones, J. Chem. Soc. (C), pp. 3577–3579, 1991.

Shohei Sakuda et al., Structure of Patulodin, A New Azaphilone Epoxide, *Produced by Penicillium urticae*, The Journal Of Antibiotics, vol. 48, No. 1, pp. 85–86, Jan. 1995.

*Primary Examiner*—Richard L. Raymond
*Attorney, Agent, or Firm*—Dechert Price & Rhoads

[57] ABSTRACT

The invention provides a method of treating or preventing a fungal infection comprising administering to a plant having a fungal infection a composition comprising an effective amount of a compound of formula I, wherein said compound is the following or an agriculturally acceptable salt of the following:

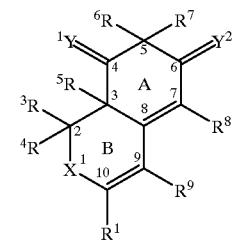

The invention further provides such compounds and related methods.

19 Claims, No Drawings

ANTIMICROBIAL AGENT FOR AGRICULTURE

This application relates to novel antimicrobials, which are particularly useful as antifungal agents, and to methods of treating or preventing microbial diseases in plants.

Since only a limited number of antifungal agents are available, efforts to identify new antimicrobial agents that are effective against fungal infections are ongoing. The relative shortage of effective antifungal agents can to some extent be attributed to the similarity between eukaryotic fungal cells and the eukaryotic cells of the organism being treated, which similarly decreases the range of possible chemotherapeutic targets that can be used to selectively kill or inhibit the fungal cells while allowing the organism's cells to continue to function.

Available antifungal pesticides include two groups of fungicides that are believed to be inhibitors of ergosterol biosynthesis. One group of compounds is N-substituted morpholines. The second group of compounds is azoles, which are believed to be inhibitors of cytochrome P-dependent 14α-demethylase. Azoles were introduced to control mildew and rusts diseases of cereals, but have a wider biological spectrum. Their use therefore extends to diseases of major agricultural crops and to the major groups of fungal pathogens, except Oomycetes which are known to be unable to synthesize sterols. Thus, there is a continuing need for fungicides with different modes of action for application to a wide spectrum of fungal pathogens. See, for example, *Biochem. Soc. Trans.* 18(1):61–62 (1990).

Further, the extensive use of fungicides with a single mode of action has resulted in the emergence of resistant fungal strains. Thus, there is a continuing need for new antifungal pesticides, especially those which have a different mode of action than the existing fungicides.

The present invention addresses the need for additional fungicides. The antimicrobials of the present invention provide a novel approach since they target a common metabolic enzyme, which instead of inhibiting the host's metabolism, appears to selectively inhibit fatty acid synthetase ("FAS") in the fungus.

SUMMARY OF THE INVENTION

The present invention provides compounds of formula I and a method of treating or preventing a fungal infection comprising administering to an organism having or at risk of a fungal infection a composition comprising an infection treating or preventing effective amount of a compound of formula I. Preferably, the organism is a plant, such as a crop plant, including corn and wheat. In the methods of the invention, a compound of the following formula I is administered:

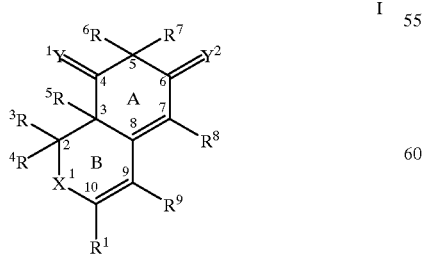

or a pharmaceutically or agriculturally acceptable salt thereof, wherein (1) $Y^1$ and $Y^2$ are independently O or S;

(2) $R^1$
  (i) is a straight-chained aliphatic group having about 2 to about 12 carbon atoms,
  (ii) the aliphatic group which additionally comprises an about 3 to about 8-membered carbocyclic ring consisting of three or more additional carbon atoms, or
  (iii) the aliphatic group which additionally comprises an about 3 to about 8-membered heterocyclic ring, wherein the heterocyclic ring contains up to 4 nitrogen atoms, up to 2 sulfur atoms, up to 2 oxygen atoms or additional carbon atoms provided the resulting heterocycle is chemically stable, (2a) wherein the carbocyclic or heterocyclic ring atoms can have 1 to 4 substituents chosen from one or more of the following groups functional groups known in the art including but not limited to fluoro, chloro, bromo, iodo, hydroxy, (C1–C6) alkoxy, (C1–C6) alkyl, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C3) haloalkyl, which can be fully or partially halogenated wherein halo is fluoro, chloro, bromo or iodo, alkanoylalkyl wherein alkanoyl is C2–C6 and alkyl is C1–C6 and the like;

(2b) wherein the non-ring portions of the straight-chained aliphatic group can be substituted with up to 4 of a (C1–C6) aliphatic group, fluoro, chloro, bromo, iodo, hydroxy, (C1–C6) alkoxy, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C6) alkyl, (C1–C3) haloalkyl, which can be fully or partially halogenated wherein halo is fluoro, chloro, bromo or iodo, or alkanoylalkyl wherein alkanoyl is C2–C6 and alkyl is C1–C6 and the like;

(3) X is oxygen or sulfur or $NR^2$;

(4) $R^2$ is hydroxy, amino which can be substituted with one or two (C1–C8) alkyl groups, (C1–C8) alkyl, (C7–C10) arylalkyl, (C1–C8) alkoxy, (C1–C8) alkanoylamino or aminocarbonyl which can be N-substituted with one or two (C1–C8) alkyl groups and the like,
  wherein $R^2$ can be substituted with up to 4 of alkylcarbonyloxy wherein alkyl can be C1–C6, alkoxycarbonyl wherein alkoxy can be C1–C6, hydroxycarbonyl, fluoro, chloro, bromo, iodo, hydroxy, (C1–C3) alkoxy, amino which can be substituted with one or two (C1–C6) alkyl groups, nitro, aminocarbonyl which can be N-substituted with one or two (C1–C6) alkyl groups, cyano, (C1–C3) alkylsulfonamido, (C1–C8) alkanoylamino, (C1–C3) haloalkylsufonamido, (C1–C3) alkyl, (C1–C3) haloalkyl, or alkanoylalkyl wherein alkanoyl is C2–C3 and alkyl is C1–C3 and the like;

(5) $R^3$ and $R^5$ either (a) represent a common oxygen forming an epoxide, (b) each represent a half bond that together forms a double bond, or (c) $R^3$ is hydrogen and $R^5$ is hydrogen, aliphatic group having 1 to 3 carbons, fluoro, chloro, bromo, iodo, nitro, cyano, hydrocarbonyl, alkylcarbonyloxy wherein alkyl can be C1–C6, alkoxycarbonyl wherein alkoxy can be C1–C6, hydroxycarbonyl, (C1–C8) alkoxy, (C1–C8) alkanoylamino, (C1–C5) alkylsulfonamido, hydroxy, amino which can be substituted with one or two (C1–C3) alkyl groups, aminocarbonyl that can be N-substituted with one or two (C1–C6) alkyl groups, (C1–C3) haloalkylsulfonamido, (C1–C3) haloalkyl, or alkanoylalkyl wherein alkanoyl is C2–C3 and alkyl is C1–C3 and the like;

(6) $R^4$ is an aliphatic group having 1 to 3 carbons, cyano, hydroxycarbonyl, alkylcarbonyloxy wherein alkyl can be C1–C6, or alkoxycarbonyl wherein alkoxy can be C1–C6, and the like;

(7) $R^8$ and $R^9$ are independently hydrogen, aliphatic group having 1 to 3 carbons, fluoro, chloro, bromo, iodo, nitro, cyano, carboxyaldehyde, hydroxycarbonyl, alkylcarbonyloxy wherein alkyl can be C1–C6, alkoxycarbonyl wherein alkoxy can be C1–C6, (C1–C8) alkoxy, (C1–C8) alkanoylamino or (C1–C5) alkylsulfonamido, and the like;

(8) $R^6$ is a (C1–C6) aliphatic group, (C6–C10) aryl, (C7–C10) aralkyl, or a (C1–C3) aliphatic group substituted with a 5 or 6-membered heteroaromatic ring having up to 4 heteroatoms comprising nitrogen, sulfur or oxygen atoms, and the like; and (9) $R^7$ is —O—$R^{10}$ or —O—(C=O)—$R^{11}$ where $R^{10}$ is a hydrogen or $R^{10}$ and $R^{11}$ are (9a) an aliphatic group with 1 to 6 carbons, which aliphatic group may be substituted with one to 3 of: hydroxy, fluoro, chloro, bromo, iodo, cyano, amino which can be substituted with one or two (C1–C3) alkyl groups, (C1–C6) alkanoylamino, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, (C1–C5) alkylsulfonate which can be partially or fully halogenated wherein halo is fluoro, chloro, bromo or iodo, (C1–C3) alkoxy, nitro, (C1–C6) alkyl, (C1–C3) haloalkyl, alkanoylalkyl wherein alkanoyl is C2–C3 and alkyl is C1–C3, or hydrocarbonyl, and the like, and wherein the aliphatic group can be substituted with an aryl or heteroaryl group where the aryl or heteroaryl moiety comprises a 6 or 10-membered aromatic ring, of which up to 4 ring atoms can be nitrogen heteroatoms, (9a1) wherein the aryl or heteroaryl group can be substituted with up to 4 substituents selected from the group consisting of (C1–C3) aliphatic group, fluoro, chloro, nitro, cyano, carboxyaldehyde, carboxyl, alkylcarbonyloxy wherein alkyl can be C1–C6, alkoxycarbonyl wherein alkoxy can be C1–C6, aminocarbonyl which can be substituted with one or two (C1–C6) alkyl groups, amino, amino substituted with one or two (C1–C3) hydrocarbons, (C1–C6) alkanoylamino, hydroxy, (C1–C3) alkoxy, amino, (C1–C3) alkylsulfonate, (C1–C3) haloalkylsufonate, (C1–C3) haloalkyl, and alkanoylalkyl wherein alkanoyl is C2–C6 and alkyl is C1–C6, and the like, or (9b) an aryl or heteroaryl group where the aryl or heteroaryl group comprises a 6 or 10-membered aromatic ring, of which up to 4 ring atoms can be nitrogen, wherein the aryl or heteroaryl group can be substituted with up to 4 substituents selected from the group consisting of (C1–C3) alkyl, (C1–C3) alkenyl, fluoro, chloro, iodo, bromo, nitro, cyano, carboxyaldehyde, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, amino, amino substituted with one or two (C1–C3) aliphatic groups, (C1–C6) alkanoylamino, carboxyl (C1–C6) ester, hydroxy, (C1–C3) alkoxy, (C1–C3) alkylsulfonamido, (C1–C3) haloalkylsulfonamido, (C1–C3) haloalkyl, or alkanoylalkyl wherein alkanoyl is C2–C3 and alkyl is C1–C3, and the like.

Preferably, in the method, when $R^7$ is acetyl the compound differs from chrysodin by at least one of (a) the presence or absence of a methylene, (b) the presence of sulfur or nitrogen in the compound in place of an oxygen, (c) the presence of halo, hydroxy, alkoxy, amino, nitro, alkanoylamino, aminocarbonyl, substituted aminocarbonyl, alkoxycarbonyl, hydroxycarbonyl, cyano, alkylsulfonamido, haloalkylsulfonamido, mono or di-alkylamino, alkanoylalkyl or hydrocarbonyl or (d) the presence in $R^1$ or $R^7$ of a carbocyclic or heterocyclic ring.

Preferably, the aliphatic groups of compound I are alkyl. Preferably, the heterocyclic ring of $R^1$ is a heteroaryl moiety. Preferably the heteroaryl moiety of $R^1$ or $R^7$ is a pyridyl, thienyl, furanyl, pyrazinyl, pyrrolyl, indolyl, pyrimidyl, thiazolyl, isothiazolyl, oxazolyl, isoxazolyl, triazolyl, tetrazolyl, quinolyl or isoquinolyl. Preferably, the carbocyclic ring of $R^1$ is a aryl moiety, which is more preferably phenyl or naphthyl. Preferably, $R^7$ includes at least one hydroxy. Preferably, $R^{10}$ and $R^{11}$ are aliphatic groups having 1 to 3 carbons, which may be substituted as set forth above. Preferably, $R^{10}$ and $R^{11}$ are substituted with at least one hydroxy. Preferably, the aliphatic group of $R^1$ has from about 2 to about 6 carbons. Preferably, the halo substituents of compound I are fluoro. Preferably, $R^3$ and $R^5$ each represent a half bond that together forms a double bond, or $R^3$ is hydrogen and $R^5$ is hydrogen.

Preferably, the alkanoylamino groups referred to above are at least C2.

Preferably, the compounds conform to formula II:

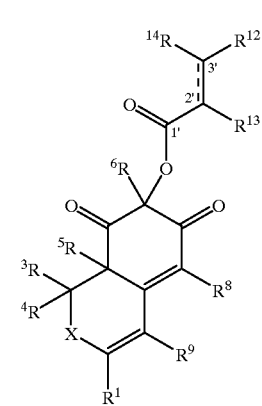

II wherein the bond indicated by the parallel solid and broken lines can be a single or double bond where, if a double bond, it can be a cis or trans double bond, wherein $R^{12}$ is aminocarbonyl which can be substituted with one or two (C1–C6) alkyl groups, hydroxycarbonyl, alkoxycarbonyl wherein alkoxy can be C1–C6, alkylcarbonyloxy wherein alkyl can be C1–C6, or trifluoromethanesulfate, $R^{13}$ is hydrogen or C1 to C3 alkyl, and $R^{14}$ is hydrogen, C1 to C3 alkyl, or hydroxy.

Preferably, the compounds conform to one of the following formulas:

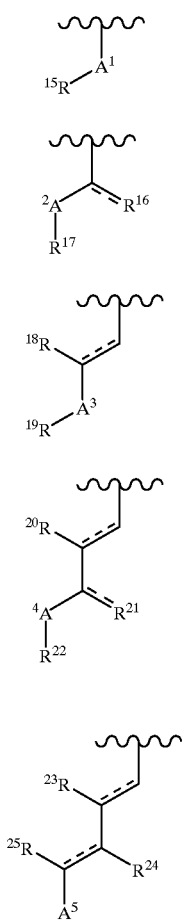

wherein the bonds represented with dashed lines are single or double bonds, $R^{15}$, $R^{17}$, $R^{19}$ and $R^{22}$ are (C1–C10) aliphatic groups, $R^{16}$, $R^{18}$, $R^{20}$, $R^{21}$, $R^{23}$, $R^{24}$ and $R^{25}$ are methyl, methylene or hydrogen, wherein $A^1$, $A^2$, $A^3$, $A^4$ and $A^5$ are six-membered aromatic or heterocyclic rings, having up to 4 nitrogen ring atoms and the rest carbon, $A^1$, $A^2$, $A^3$, $A^4$ and $A^5$ can be substituted with up to 4 substituents selected from the group consisting of fluoro, chloro, bromo, iodo, nitro, cyano, amino, (C1–C3) mono or di-alkylamino, (C1–C8) alkanoylamino, (C1–C3) alkylsulfonamido, (C1–C3) haloalkylsulfonamido which can be fully or partially halogenated wherein halo is fluoro, chloro, bromo or iodo, aminocarbonyl which can be substituted with one or two (C1–C6) alkyl groups, alkylcarbonyloxy wherein alkyl can be C1–C6, (C1–C6) alkoxycarbonyl, hydroxycarbonyl, (C1–C3) haloalkyl, which can be fully or partially halogenated wherein halo is fluoro, chloro, bromo or iodo, hydroxy, (C1–C8) alkoxy, and alkanoylalkyl wherein alkanoyl can be C2–C3 and alkyl can be C1–C3, and wherein the dashed lines indicate bonds that are either double or single bonds. Preferably $R^{15}$, $R^{17}$ $R^{19}$ and $R^{22}$ include an unsaturated bond conjugated to another unsaturated bond. Preferably, the illustrated two bonds linking $A^1$, $A^2$, $A^3$, and $A^4$ are meta to each other. Preferably, at least one of the dashed lines in each of formulas III–VII represents a double bond.

In the methods of treatment or prevention, preferably the microbial infection is a fungal infection in a plant, such as infections caused by fungi of the genus Oomycetes, fungi of the genus Trichoderma, including *Trichoderma reesei,* fungi of the genus Alternaria, including *Alternaria solani* and *Alternaria brassicicola,* fungi of the genus Fusarium, including *Fusarium oxysporum, Fusarium acuminatum,* fungi of the genus Ascobolus, including *Ascobolus crenulatus,* fungi of the genus Phoma, including *Phoma medicaginis,* fungi of the genus Rhizoctonia, including *Rhizoctonia solani,* fungi of the genus Pythium, including *Pythium ultimum,* fungi of the genus Cladosporium, including *Cladosporium cucumerinum,* fungi of the genus Truncatella, including *Truncatella hartigii,* fungi of the genus Septoria, including *Septoria tritici,* fungi of the genus Helminthosporium, including *Helminthosporium oryzae,* fungi of the genus Aspergillus, including *Aspergillus niger,* fungi of the genus Botrytis, including *Botrytis cinerea,* fungi of the genus Rhizopus, including *Rhizopus stolonifer* and fungi of the genus Nectria, including *Nectria heamatococca.*

In the methods of treatment or prevention, preferably the infecting microbe expresses fatty acid synthetase and the plant is treated with a composition comprising an amount of a compound of formula I effective to inhibit the expressed fatty acid synthetase.

Preferably, the pharmaceutical composition includes an agriculturally acceptable diluent or excipient.

In one aspect, the present invention provides a method of treating or preventing a microbial disease comprising (a) combinatorially generating compounds by contacting a first compound according to formula I, excepting that $R^7$ is replaced by $R^{29}$, which differs from $R^7$ only in encompassing —OH, (i) with two or more second compounds that share a functionality that is expected to be reactive with the first compound or (ii) separately with two or more concentrations of a third compound having a functionality that is expected to be reactive with the first compound, (b) identifying among the generated compounds a selected compound or selected pool of compounds having relatively greater antimicrobial activity, and (c) administering the selected compound or pool to a plant to treat or prevent a microbial infection, wherein the contacting of step (a) occurs under conditions suitable for the reaction of the first compound with the reactive functionalities of the second or third compounds. Preferably, the second compounds are acylating agents. Alternatively, the second compounds are alkylating agents. In another alternative, the first compounds are according to formula VIII and the second compounds are amines. In another alternative, the first compound has a O at position 1 and the second compounds are O-alkylhydroxyamines. In another alternative, the first compound has a O at position 1 and the second compounds are carbazates which may be substituted. In another alternative, the third compound is hydrogen. Preferably, the method further comprises the step of assaying two or more pools of compounds for the ability to inhibit a microbial FAS, wherein each pool comprises one or more of the generated compounds from the contacting step.

For the purposes of this application, the fused ring structure shared by formulas I and II shall be referred to as the "AB ring", the individual rings referred to as the A and B rings, as indicated, and the ring positions shall be numbered as indicated.

DEFINITIONS

The following terms shall have the meaning set forth below:

antifungal agent
  an antimicrobial agent that acts on one or more strains of fungi.

antimicrobial agent
  a biological agent that inhibits the reproduction or decreases the survival of pathogenic microbial cells or inhibits the propagation, which includes without limitation replication, viral assembly or cellular infection, of a virus.

antimicrobial effective amount
  an amount of an antimicrobial agent administered to an organism infected with a microbe which is effective to reduce the rate at which the microbe reproduces or to reduce the population of the microbe in the organism.

biological agent
  an agent that is useful for diagnosing or imaging or that can act on a cell, organ or organism, including but not limited to drugs (pharmaceuticals) to create a change in the functioning of the cell, organ or organism.

FAS inhibiting effective amount
  an amount of an antimicrobial agent effective (a), for a systemic infection, to produce a systemic concentration in the treated plant of the antimicrobial agent effective in vitro to create a statistically significant inhibition of the FAS of the infectious organism or (b), for nonsystemic infections, to produce a localized concentration of the antimicrobial agent effective in vitro to create a statistically significant inhibition of the FAS of the infectious organism. The in vitro assay used measures the synthesis of fatty acids at pH 6.6, at a temperature of 25° C., in the presence of 500 $\mu$M NADPH, 500 $\mu$M malonyl CoA, 20 $\mu$M acetyl CoA and appropriate buffers and salts.

microbe
  a bacteria, mycoplasma, fungi including but not limited to yeast, virus, protozoa or parasite (such as a malaria parasite).

DETAILED DESCRIPTION

The invention provides a family of compounds according to the basic formula:

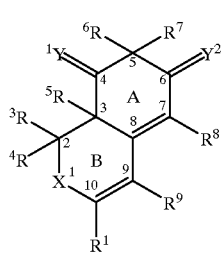

I

The substituents for this formula are as described above. The family includes the following compound A and compound B:

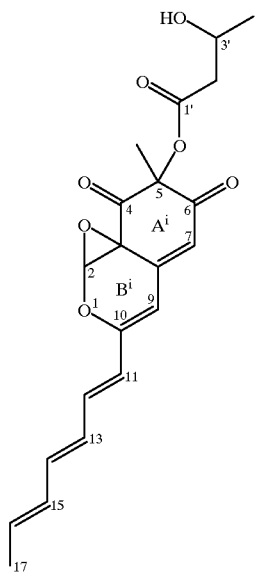

A

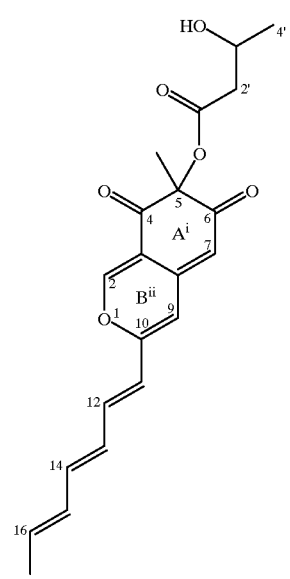

B

Compound A and Compound B have been isolated from a fungal cell line as described in Example 1. These compounds are useful as starting material to synthesize compounds within the above-described family of compounds of the invention.

Epoxides such as compound A can be deoxygenated for example to obtain compound B by a number of means known to the art, including treatment with the following deoxygenation reagents: (a) $WCl_6$ and n-BuLi; (b) $Ph_3P$; (c) $(EtO)_3P$; or (d) $H_2NCSNH_2$.

The acyl substituent at the 5 position of the $A^i$ ring can be removed by several methods known to the art including (1) treatment a strong base such as a metal alkoxide in an alcoholic solvent or, in the case of compound B, (2) oxidation of the exposed alcohol functionality at the 3' position to a ketone, for instance using a mixture of oxalyl chloride, dimethylsulfoxide (DMSO) and triethylamine, followed by reaction with phenyl hydrazine. The thus exposed hydroxyl group at the 5 position can then be acylated or alkylated by known means.

Note, that the discussion herein focuses on compound A or compound B as a model for describing chemical protocols. Those of ordinary skill in the art will recognize that these protocols are applicable to others of the compounds within the genus described above.

When the hydroxyl at the 3' position of compound B is oxidized to a ketone, this ketone can be reacted with triflic anhydride ($Tf_2O$) or N-phenyl triflamide (PhNHTf) in a mixture of an aprotic solvent and a base such as pyridine or triethylamine to form a —O—CO—C=C(OTf)($CH_3$) structure at the 5 position of the $A^i$ ring. The compound containing this —O—CO—C=C(OTf)($CH_3$) structure can be reacted in an alcoholic solvent or in a mixture of a solvent alcohol (ROH) and a dipolar, aprotic solvent such as dimethyl formamide (DMF) with carbon monoxide and catalytic amounts of palladium salts in the presence of 1,3-bis (diphenylphosphinopropane) to convert the structure to —O—CO—C=C(COOR)($CH_3$), where R is from the solvent alcohol ROH. The ester function of the —O—CO—C=C($CO_2R$)($CH_3$) structure can be hydrolyzed by known methods to create a carboxylic acid that can serve as starting material for additional side chain modifications. For instance, the acid functionality can be reacted, using a condensation reagent such a dicyclohexyl carbodiimide, with an amine compound to form an amide. Such amine compounds can, of course, carry additional functionalities, such as protected carboxylic acid moieties.

The substituent at the 5 position of the $A^i$ ring of the B compound can be converted to a —O—CO—CH=CH—$CH_3$ by reacting the B compound with methane sulfonyl chloride in a solvent containing base.

The oxygen of the $B^{ii}$ ring of compound B can be substituted with an amine nitrogen by reacting compound B with an amine compound, such as without limitation, alkyl amine, O-alkylhydroxyamine, an amino acid, and t-butylcarbazate. The alkyl amine, alkylhydroxyamine and t-butylcarbazate ($NH_2NHCO_2$-tBu) reactions form the following compounds, respectively:

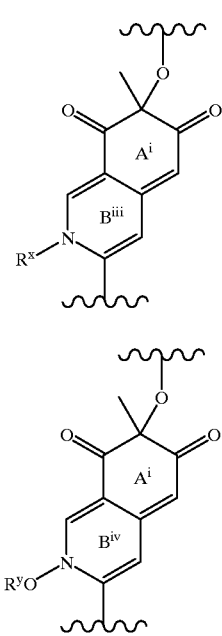

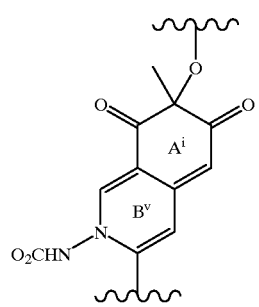

The $CO_2$ moiety of formula 3 can be removed with acid, exposing a hydrazine functionality that can be used to attach electrophilic reagents such as acid chlorides.

The oxygen of the $B^{ii}$ ring of compound B can be converted to a sulfur by reaction with sodium sulfide under strongly basic conditions, for example in the presence of potassium t-butoxide. The carbonyls at positions 4 and 6 of compound B can be converted to the corresponding thiocarbonyls by reaction in an inert solvent with Lawesson's reagent according to standard procedures. The $A^i$ or the $B^{ii}$ rings of compound B can be substituted for instance by reaction with a mixture of DMF and phosphorous oxychloride under standard Vilsmeier conditions, or with preformed N,N-dimethylchloroiminium chloride in a suitable solvent.

The 5-position of the A ring can define a chiral center. Both stereoisomeric forms of this chiral center are within the invention. When an epoxide is formed between the 2 and 3-position of the B ring, two stereoisomeric forms are possible; both such forms are within the invention.

The compounds of the invention provide useful starting points for combinatorial chemistry approaches to identifying particularly effective antimicrobial compounds which are then used to treat or prevent infections. The most common combinatorial approach creates numerous pools of related compounds, where each pool contains a different set of such compounds. Typically, the pools are created by reaction schemes that yield multiple related compounds. The pools are assayed for a useful characteristic and pools containing compounds with this characteristic are identified. The known information on the contents of these pools is then used to either prepare a library of potentially useful compounds or to design more focused combinatorial pools of compounds. The library of compounds or the new combinatorial pools are then tested for the useful characteristic. Eventually, by this process of elimination specific compounds having the useful characteristic are identified.

For one example of the combinatorial approach, the compounds defined by the formula 4 below can be reacted with mixtures of various acyl chlorides to create pools of compounds having different acyl groups at the 5 position of the $A^{ii}$ ring.

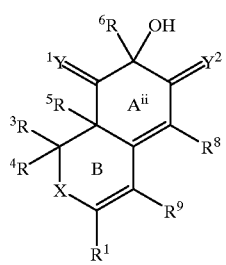

Examples of the acyl chlorides that can be used include without limitation acetyl chloride, benzoyl chloride, halo-acetyl chloride, halo-benzoyl chloride, phenylacetyl chloride, 3-cyclohexylpropanoyl chloride, isovaleryl chloride, 2-napthoylacetyl chloride, 6-phenylhexanoyl chloride, and 3-fluoropropionyl chloride. These pool-forming reactions could, for instance, be conducted in THF with 1.0 mmol of compound 4, 1.1 mmol pyridine and 0.1 mmol of each of a number (e.g., 10) of acyl chlorides. The reaction mixtures can further include 4-dimethylaminopyridine (e.g., 0.1 to 1.0 mmol) as a catalyst.

Alternatively, the compounds of formula 4 can be reacted with alkylating reagents in the presence of a strong proton extraction agent such as potassium t-butoxide to form compounds having various ether attachments at the 5 position of the $A^{ii}$ ring. Examples of such alkylating reagents include without limitation methyl iodide, ethyl triflate, propyl mesylate, phenethyl iodide, 4-cyclohexybutyl triflate, 3-methylbenzyl bromide, 4-methoxybenzyl bromide, chloromethyl methyl ether, 4-methoxybutanyl triflate and isopropyl triflate.

In another example of a combinatorial approach, mixtures of amine compounds are reacted with compounds of formula 5 illustrated below, to substitute amine or substituted amines at the position of the ring oxygen.

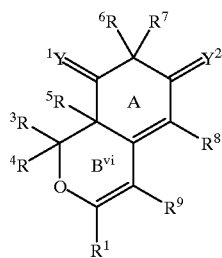

Examples of such amines include without limitation ammonia, methylamine, n-propylamine, cyclohexylmethylamine, benzylamine, 4-chlorobenzylamine, 3-trifluoromethylphenethyl amine, 4-phenylbenzylamine, phenethylamine and sec-pentylamine.

Another combinatorial approach would take compounds of the invention and hydrogenate in the presence of, for instance, a palladium, platinum, rhodium or nickel catalyst using various ratios of hydrogen gas designed to eliminate various numbers of double bonds.

The antimicrobial agent of the invention can be administered to a plant, for example, as a powder, pellet, liquid suspension or liquid solution. The antimicrobial agent of the invention can be administered alone, or it can be combined with an agriculturally acceptable carrier or excipient according to standard agricultural practice. The antimicrobial agent can be applied to the plants such as crops in a field, for example, by spraying, air dropping or irrigation feeding. The antimicrobial agent can be applied to the leaves, flowers, stems, roots or seeds of the plant. Further, the antimicrobial agent may be administered, for example, by combination with a fertilizer and optionally other pesticides and applied to the crops or other plants. Preferably, the antimicrobial agent is mixed with or alternated with agents such as fungicides with different biochemical modes of action to avoid development of resistant strains. See, for example, *Biochem. Soc. Trans.* 18(1):61–62 (1990), which is hereby incorporated by reference herein in its entirety. The antimicrobial agent can be administered prophylactically or as a treatment of an existing infection. Preferably, the antimicrobial agent is at least administered during the most disease-prone growth of the plant during time periods in which the environmental conditions are favorable for infection. More preferably, the antimicrobial agent is administered more than once during a growth period. See, for example, *Hindustan Antibiot. Bull.* 12(1):22–25 (1969), which is hereby incorporated by reference in its entirety. Preferably, the antimicrobial agent is used in amount effective to treat or prevent microbial infection, such as an amount effective to prevent fungal spore germination. The amount of antimicrobial agent used will differ depending upon the identity of the microbe and the type of plant treated. Preferably, the antimicrobial agent is applied in an amount ranging from about 1 g/1000 ft$^2$ to about 1 kg/1000 ft$^2$.

Experiments described below in Example 1 have shown that compound B is not directly inhibitory of FAS using the in vitro assay described below. However, cell extracts made after exposure to compound B have markedly reduced FAS activity. Without limiting the invention to theory, it is believed that compound B is metabolized to a form that inhibits FAS.

The antimicrobial agents of the invention are suitable for use in plants, including crop plants such as corn, wheat, sorghum and soybeans, and fruits, vegetables, flowering plants, grasses, shrubs and trees.

In certain embodiments, compounds that can be used according to the invention include the following compounds:

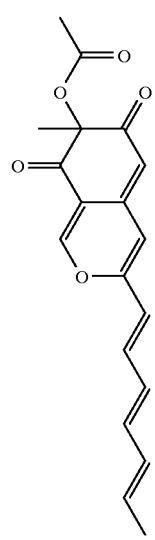

6

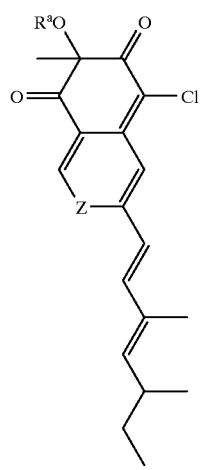

8

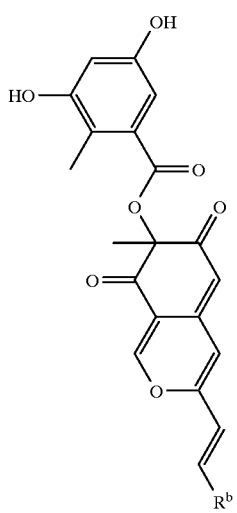

9

7

In other embodiments, the compounds differ from the above compounds. In the above formulas, $R^a$ represents hydrogen, acetyl, 2-methyl-3,5-dihydroxyphenylcarbonyl or methyl, Z represents oxygen or NH, and $R^b$ is methyl, hydroxymethyl or carboxyl. Formula 7 describes chrysodin. Formula 8 describes patulodin. Formula 9 describes sclerotiorin and related compounds. Formula 10 describes mitorubicin and related compounds. In certain embodiments, when $R^7$ of formula I is acetyl, the compound of the invention differs from chrysodin by at least one of (1a) the presence or absence of a methylene, (1b) the presence of sulfur or nitrogen in the compound in place of an oxygen, (1c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde or (1d) the presence in $R^1$ or $R^7$ of a carbocyclic or heterocyclic ring. In some embodiments, when $R^7$ is 2,4-dihydroxypentyl the compound of the invention differs from patulodin by at least one of (2a) the presence or absence of a methylene, (2b) the presence of sulfur or nitrogen in the compound in place of an oxygen, (2c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde, (2d) the presence in $R^1$ or $R^7$ of a carbocyclic or heterocyclic ring or (2e) the absence of an epoxide moiety. In certain embodiments, the difference recited in (1a) and (2a) is at least two methylenes. In some embodiments, either the 7-position of the A ring is not substituted with chloro or the $R^1$ position differs from a 3,5-dimethyl-hepta-1,3-dienyl group. In certain embodiments, $R^7$ is either (a) not one of 2-methyl-3,5-dihydroxy-phenylcarbonyl or methyl or (b) $R^1$ is not one of propyl-2-enyl, 1-hydroxypropyl-2-enyl or 1-carboxyl-ethylenyl.

The invention is further explained by reference to the following non-limiting examples.

EXAMPLE 1

Isolation of Compound A and Compound B

EXAMPLE 1A

Isolation Procedures

An inoculant of microorganism CK2108, which is a *Penicillium solitum* Westling fungus deposited with the American Type Culture Collection in a deposit pursuant to the Budapest Treaty under Accession No. 74361 was fermented in 25 mls of a seed broth at 28° C. for two days. Each 1 L of the seed broth was formulated as follows:

| | |
|---|---|
| Glucose | 20.0 g |
| PHARMAMEDIA | 15.0 g |
| (Traders Oil Mill Co., Ft. Worth, TX) | |
| $(NH_4)_2SO_4$ | 3.0 g |
| $ZnSO_4 \cdot 7H_2O$ | 0.03 g |
| $CaCO_3$ | 4.0 g |
| Yeast extract | 5.0 g |
| $H_2O$ | to 1 L |

The overnight inoculant was used to inoculate 3 liter of broth according to the following formula:

| | |
|---|---|
| Glucose | 20.0 g |
| Sucrose | 50.0 g |
| PHARMAMEDIA | 20.0 g |
| (Traders Oil Mill Co., Ft. Worth, TX) | |
| $NaNO_3$ | 1.0 g |
| $K_2PO_4$ | 0.5 g |
| KCl | 0.7 g |
| L-histidine | 1.0 g |
| $MgSO_4 \cdot 7H_2O$ | 0.014 g |
| $H_2O$ | to 1 L |

The 3-liter culture was fermented for 5 days at 28° C. The fermentation was then extracted with 7.5 liters of ethyl acetate. The organic extract was dried to yield 12.36 g of crude extract.

400 mg of crude extract was processed using a coil planet centrifuge ("CPC"), an apparatus for conducting countercurrent chromatography ("CCC") marketed by P. C. Inc. of Potomac, Md. Two solvent phases were formed from 1:4:4:4 of n-hexane: ethyl acetate: methanol: water. 400 mls of the lower phase were loaded into the coil of the CPC to form the stationary phase. The extract was mixed with 9 mls of the two-phase mixture of solvents and the soluble components (217 mg) were injected into the CPC. The coil was then rotated to hold the stationary phase in place while the upper phase solvent was pumped through the coil at 3 ml/min. Elution was monitored by absorbance at 270 nm. Two major peaks, a first eluting peak (48 mg) and second eluting peak (10 mg), were observed. The first eluting peak had activity as tested by the MIC assay of Example 1B; the second eluting peak was more active on a weight basis than the first. The first eluting peak also had activity in the enzyme inhibition assay of Example 1C.

The two components were separately fractionated using reverse-phase liquid chromatography on a 10×250 mm C18 column from Merck (Darmstadt, Germany). The flow rate used was 10 ml/min. The solvent program started with 70% water, 30% acetonitrile. A 25 minute linear gradient to 100% acetonitrile was initiated at injection. The sample (5 mg) was injected in 50 μl DMSO. Fractions were collected each ½ minute. Elution was monitored by absorbance at 270 nm. The material from the first eluting peak from the CPC displayed one major peak that eluted in fractions 25–27. This material "compound A" retained activity in the MIC assay of Example 1B and the enzyme inhibition assay of Example 1C. The material from the second eluting peak from the CPC displayed one major peak that eluted in fraction 23. This material "compound B" retained activity in the MIC assay of Example 1B.

NMR analysis such as that described in Example 1D, suggested the insoluble material from the CPC separation was substantially compound A.

EXAMPLE 1B

MIC assay

The fractions from the purification were tested for antifungal activity against *C. albicans* (strain B311A available from Dr. Paul Actor, Temple University and strains ATCC Nos. 10231 and 10261) and *C. tropicalis* (strain 13803). Fungi were grown in 1× yeast nitrogen broth ("YNB") medium (BBL, Cockeysville, Md.) containing 15 μg/ml asparagine and 100 μg/ml kanamycin. Prior to the assay for antifungal activity, the fungus to be tested for susceptibility was grown overnight from a single colony in 5 ml of medium at 30° C. This overnight culture was diluted 1:10 with fresh medium and grown at 37° C. for 4 hours. A volume of 5 μl of extracts, dissolved in DMSO, was added to each separate well in a series of 96-well plates. 4,000 fungal cells were then added to each plate in 95 μl of medium. The optical densities of the wells were measured and the plates incubated at 37° C. The optical densities were again measured after 24 and 48 hours. Minimum inhibitory concentrations ("MICs") for the extracts were determined using this procedure wherein the extracts were serially diluted in medium prior to mixing with the 4,000 fungal cells.

Using the procedure described in the previous paragraph, it was determined that the MICs for compound A and compound B against *Candida Albicans* strain B311A grown in YNB medium were 25 μg/ml and 6.25 μg/ml, respectively. When Sabouraud Dextrose Broth (Difco, Detroit, Mich.) was substituted for YNB medium, the MIC value for each compound was 50 μg/ml.

EXAMPLE 1C
FAS inhibition assay

To test the compounds for FAS inhibitory activity, an FAS extract from *Saccharomyces cerviseae* was prepared. Freeze dried yeast (Fleishmans' freeze dried yeast, Specialty Brands, San Francisco, Calif.) 1 g, was hydrated in 5 mls deionized water for 15 minutes at 4° C. Subsequent extraction steps were conducted at a temperature between 4° C. and 10° C., except that in the cell lysis step the temperature may have briefly exceeded these boundaries. The cells were pelleted by centrifugation; the pelleted volume was measured; and the cells were resuspended in 5 vol. (5 mls per ml cell volume) extraction buffer [125 mM KH2PO4, pH 6.6, 1 mM EDTA, 1 mM DTT, 0.7 µg/ml pepstatin (Boehringer Mannheim, Indianapolis, Ind.), 0.2 µg/ml aprotinin (Boehringer Mannheim, Indianapolis, Ind.), 0.2 µg/ml leupeptin (Boehringer Mannheim, Indianapolis, Ind.)]. The cells were again pelleted and resuspended in 2 vol. extraction buffer. The cells were lysed using a bead mill homogenizer (Biospec Products, Bartlesville, Okla.) with a volume of glass beads equal to the volume of the yeast cells. The bead mill was operated five times for 1 minute, with 1 minute intervals between operations to allow the water jacket of the bead mill to cool the material in the mill. The lysate was centrifuged at 30,000×g for 30 minutes and the supernate was collected. Ammonium sulfate was added to the supernate to 50% saturation and the mixture was stirred for 30 minutes on ice. The precipitate was collected by centrifugation (10,000×g, 10 min) and dialyzed against three changes of dialysis buffer (125 mM $KH_2PO_4$, pH 6.6, 1 mM EDTA, 1 mM DTT, 3 mM sodium azide) and the dialyzed material collected as the "FAS extract."

105 µl of FAS extract was placed in each well of a polypropylene 96 well plate (Costar Corp. Cambridge, Mass.) and multiple 5 µl dilutions of compound A, compound B or negative control solution were introduced into each of the wells. Following this, the plate was incubated at room temperature for 30 minutes. Duplicate alloquots of 50 µl from each well were transferred into separate wells of a 96-well PolySorp micotiter plate (Nunc, Denmark). Into each well of the PolySorp plate, were added simultaneously 50 µl of freshly prepared 2× assay cocktail (a mix of: 833 µl 3M $K_2HPO_4$, pH 6.6; 1 ml 10 mM NADPH (Sigma Chemical Co., St. Louis); 1 ml 10 mM malonyl-CoA (Sigma); 40 µl 10 mM acetyl-CoA (Sigma); 20 µl 1M DTT (Sigma); 7.1 ml deionized water). The relative initial reaction rates in each well were measured by measuring the decrease in optical density at 340 nm using a UV Max microtiter plate reader (Molecular Devices, Sunnyvalle, Calif.).

Using the above-described method, compound A was found to inhibit FAS from *S. cereviseae* with an $IC_{50}$ of 160 µg/ml.

EXAMPLE 1D
Structural Analysis

Mass spectroscopy determined that compound A had a molecular formula of $C_{21}H_{22}O_7$ and compound had a molecular formula of $C_{21}H_{22}O_6$. Compound B was analyzed by a homonuclear ($^1H$—$^1H$) COSY 2-D NMR experiment. The COSY data indicated a spin system having three trans double bonds (C11–C17) and another comprising a hydroxypropyl group (C2'–C4'). A heteronuclear multiple quantum coherence experiment was used to align the hydrogen atoms indicated by $^1H$-NMR with carbon atoms indicated by $^{13}C$-NMR. The combined NMR data implied the structure indicated above in the Detailed Description. Once this structural determination was made, it was quickly determined that the NMR data for compound A implied the structure indicated above in the Detailed Description.

Compound A showed 1H-NMR and $^{13}C$-NMR spectra having peaks as indicated in the Table below. It is believed that the peaks can be assigned to particular carbons or to hydrogens attached to particular carbons as indicated in the Table.

| C/H # | $^1H$ | $^{13}C$ |
|---|---|---|
| 2 | 5.89 s | 82.07 |
| 3 | — | 55.54 |
| 4 | — | 197.39 |
| 5 | — | 85.84 |
| 5-CH₃ | 1.62 s | 22.21 |
| 6 | — | 192.51 |
| 7 | 6.28 m | 120.71 |
| 8 | — | 146.71 |
| 9 | 6.11 s | 105.37 |
| 10 | — | 154.49 |
| 11 | 6.19 d, J = 15.2 | 123.77 |
| 12 | 6.95 dd, J = 15.1, 11.3 | 136.68 |
| 13 | 6.31 dd, J = 14.9, 11.4 | 129.93 |
| 14 | 6.56 dd, J = 14.8, 10.8 | 139.82 |
| 15 | 6.22 m | 132.6 |
| 16 | 5.94 m | 134.52 |
| 17 | 1.79 dd, J = 6.7, 0.6 | 18.57 |
| 1' | — | 171.09 |
| 2' | 2.52 dd, J = 14.3, 7.0 | 43.17 |
|   | 2.42 dd, J = 14.4, 6.0 |   |
| 3' | 4.11 m | 64.92 |
| 4' | 1.20 d, J = 6.2 | 23.21 |

EXAMPLE 2
Disk diffusion assay for antimicrobial activity

Fungal cells were grown overnight from a single colony in 2–5 ml Sabouraud Dextrose Broth at 37° C. 1–5×10⁶ were spread onto Sabouraud Dextrose Agar plates (Difco, Detroit, Mich.). Sterile 6 mm filter disks were evenly spaced with at least about 22 mm separation on the plates. To each disk, 100 µg of a compound to be tested was applied in 5–10 µl DMSO. On each plate, two disks containing 2.5 and 10 µg, respectively, of Amphotericin B (Sigma) and two disks containing 2.5 and 10 µg, respectively, of cerulenin (Sigma) were used as positive controls. A disk containing only DMSO served as the negative control. The plates were incubated at 37° C. for 24 hours and the zone of growth inhibition about each disk was visually examined and measured. Compound A and compound B typically produced clear zones of 8–12 mm diameter. Amphotericin B typically produced a clear zone of 8–10 mm diameter. Cerulenin typically produced a hazy zone of 20–25 mm diameter. A clear zone is indicative of fungicidal activity, while a hazy zone is indicative of fungistatic activity.

By this method, compound A and compound B had antimicrobial activity against *Candida albicans* (strains ATCC 10231 and ATCC 10261), *Candida tropicalis* (strain ATCC 13803) and two strains of *Fusarium acuminatum* (strains ATCC 32965 and ATCC 32966).

EXAMPLE 3
In vivo activity of Compound A and Compound B

In vivo activity was determined using a murine systemic model of candidiasis. Groups of 5 to 10 mice were inoculated IV with 1–2×10⁷ cells of *C. albicans* strain ATCC 10231 (10 times the lethal dose). One hour after inoculation, the candidate antifungal compounds were delivered IP. 10 mg/kg of compound A was injected into each mouse of the compound A treatment group. Two separate treatment groups received 30 and 100 mg/kg, respectively, of compound B. Amphotericin B was injected into a positive control treatment group at 10 mg/kg. All compounds were delivered in phosphate-buffered saline (PBS) and one treatment group received PBS. Twice daily thereafter the mice were observed, the number of dead mice recorded, and the dead mice removed. After nine days, the total mortality over the period was determined.

Using the same methodology, it was determined that the maximal tolerated dose in these mice (i.e., the maximum dose that caused no deaths within 72 hours following IP administration) of compound B was in excess of 200 mg/kg. The mice treated with 2108B or Amphotericin B injected IP in 20 ml of phosphate buffered saline, pH 7.4 had the following treatment profiles:

| treatment compound | Dose mg/kg | Deaths Each Day Post Inoculation | | | | | | | | | | % Survival |
|---|---|---|---|---|---|---|---|---|---|---|---|---|
| | | 0 | 1 | 2 | 3 | 4 | 5 | 6 | 7 | 8 | 9 | |
| vehicle | — | 0 | 1 | 1 | 0 | 1 | 1 | 1 | 0 | 0 | 0 | 0 |
| Compound B | 100 | 0 | 2 | 0 | 0 | 0 | 0 | 0 | 0 | 1 | 0 | 40 |
| Compound B | 30 | 0 | 2 | 1 | 0 | 0 | 0 | 0 | 0 | 0 | 0 | 40 |
| Amphotericin B | 10 | 0 | 0 | 0 | 0 | 1 | 0 | 0 | 0 | 0 | 0 | 80 |

Using the methodology described above, the maximum tolerated dose for compound A was 10 mg/kg. As indicated by the results below, this particular compound is more suitable for treating non-systemic infections in mice due to the low maximum tolerated dose.

| treatment compound | Dose mg/kg | Deaths Each Day Post Inoculation | | | | | | | | | | % Survival |
|---|---|---|---|---|---|---|---|---|---|---|---|---|
| | | 0 | 1 | 2 | 3 | 4 | 5 | 6 | 7 | 8 | 9 | |
| vehicle | — | 0 | 0 | 0 | 3 | 0 | 0 | 2 | 0 | 0 | 0 | 0 |
| Compound A | 10 | 0 | 0 | 2 | 3 | 0 | 0 | 0 | 0 | 0 | 0 | 0 |
| Amphotericin B | 10 | 0 | 0 | 1 | 0 | 0 | 0 | 0 | 0 | 0 | 0 | 80 |

EXAMPLE 4

Comparative results

Strain 2108 was also determined to produce patulodin, as determined by NMR and mass spectroscopy. The structure of patulodin is as follows:

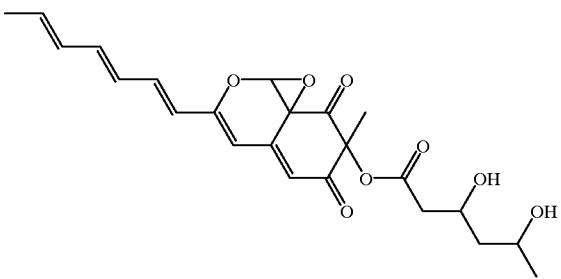

Using the test for antifungal activity set forth in Example 1B, the MIC for this compound against *Candida albicans* B311A was determined to be in excess of 100 μg/ml, which value is substantially higher than the values of 25 μg/ml and 6.25 μg/ml determined for compound A and compound B, respectively. Additionally, in the disk diffusion assay of Example 2, the zone of inhibition was 7 mm, barely larger than the disk itself.

EXAMPLE 5

Conversion of Compound A to Compound B

A dry 250 ml round bottom flask was flushed with nitrogen, charged with 60 ml of dry THF, and cooled to −78° C. Tungsten hexachloride 2.27 g, 5.74 mmol) was introduced into the flask. While the cold suspension was stirred, 7.18 ml (11.48 mmol) of 1.6M n-BuLi in hexane was added slowly. The resulting mixture was warmed to room temperature over two hours. The mixture was recooled to −78° C. and compound A (1.09 g, 2.82 mmol) was introduced. The cooling bath was removed and the mixture was stirred for 45 minutes and then poured into an aqueous sodium tartrate solution (prepared by dissolving 4.5 g, 30 mmol, of tartaric acid in 20 ml of 2N aqueous NaOH). This mixture was transferred to a separatory funnel, to which ethyl acetate (300 ml) and water (100 ml) were also added. The aqueous layer was extracted with additional ethyl acetate (2×100 ml) and the combined organic layers were washed with a brine solution (100 ml) made basic with 50 ml of 2N NaOH. The organic layer was dried over $MgSO_4$, filtered and evaporated to give a brown viscous oil. This material was purified by column chromatography on 64 g of silica gel, which was eluted with 65% ethyl acetate, 34% hexane, and 1% methanol. A small amount of nonpolar material eluted first followed by a fraction corresponding to starting material (85 mg) and finally the desired product (279 mg).

The compound B prepared by this process had the same physical properties, in terms of TLC $R_f$, HPLC retention time, UV spectra, $^1H$ NMR spectra and mass spectra, as the natural product. The HPLC protocol used a 10×100 mm $C_{18}$ reversed-phase column from Merck (Darmstadt, Germany). The column was equilibrated with 95% $H_2O$, 5% $CH_3CN$ and developed with a 25 minute linear gradient to 100% $CH_3CN$. The mass spectra showed major ion peaks at 393.4 $(M+Na^+)$, 371.4$(M+H^+)$, 198.3 and 166.3 m/e.

EXAMPLE 6

Additional conversions of Compound A to Compound B

Reaction A. Compound A was converted to compound B using $WCl_6/2$ n-BuLi according to the method of Umbreit and Sharpless, *Organic Synthesis Coll.* Vol. VII, p. 121. A dry 25 mL round bottom flask was flushed with nitrogen, charged with dry THF (4.0 mL), and cooled to −78° C. Tungsten hexachloride (148 mg, 0.37 mmol) was introduced. While the cold suspension was stirred, 1.6M n-BuLi in hexane (0.46 mL, 0.74 mmol) was added slowly. The resulting mixture was stirred for 0.5 hour before warming to room temperature for 0.5 hour. The mixture was recooled to −78° C. and compound A (77 mg, 0.20 mmol) was introduced. The cooling bath was removed and the mixture was stirred for 90 minutes and then poured into a separatory funnel containing a saturated aqueous potassium sodium tartrate solution (20 mL) made basic with 2M NaOH (20 mL). This mixture was extracted with chloroform (3×25 mL). The combined organic layers were washed with a brine solution (100 mL) and dried over MgSO4. After filtration, rotary evaporation afforded a brown viscous oil.

For this reaction and reactions B, C and D, described below, product was isolated by reversed-phase HPLC on a Merck 10×250 mm $C_{18}$ column (Darmstadt, Germany). The column was equilibrated with 95% $H_2O$, 5% $CH_3CN$ and developed with a 25 minute linear gradient to 100% $CH_3CN$. Mass Spectroscopic analysis of the product eluting at between 13 and 15 minutes confirmed the presence of compound B.

Reaction B. Compound A was converted to compound B using $Ph_3P$ according to the method of Yamada et al., *J. Org. Chem.* 43: 2076, 1976. A dry 25 mL round bottom flask was flushed with nitrogen, charged with compound A (77 mg, 0.2 mmol), dry benzene (5.0 mL), and triphenylphosphine (53 mg, 0.2 mmol). The resulting solution was warmed to reflux and stirred overnight. The reaction mixture was cooled, and solvent was removed by rotary evaporation leaving a brown viscous oil. Mass Spectroscopic analysis of the product eluting from the reversed-phase HPLC column at between 13 and 15 minutes confirmed the presence of compound B.

Reaction C. Compound A was converted to compound B using $(EtO)_3P$ according to the method of Scott, *J. Org. Chem.*, 22: 1118, 1957. A dry 25 mL round bottom flask was flushed with nitrogen, charged with compound A (77 mg, 0.2 mmol), dry benzene (5.0 mL), and triethyl phosphite (34 uL, 0.2 mmol). The resulting solution was warmed to reflux and stirred overnight. The reaction mixture was cooled, and solvent was removed by rotary evaporation leaving a brown viscous oil. Mass Spectroscopic analysis of the product eluting from the reversed-phase HPLC column at between 13 and 15 minutes confirmed the presence of compound B.

Reaction D. Compound A was converted to compound B using $H_2NCSNH_2$, $NaHCO_3$ and $Ph_3P$ according to the method of Goldbach, et al., *J. Chem. Soc. Chem. Comm.* 1987, pp. 1434 et seq. A dry 25 mL round bottom flask was flushed with nitrogen, charged with compound A (77 mg, 0.2 mmol), dry benzene (5.0 mL), sodium bicarbonate (25 mg 0.3 mmol), thiourea (15 mg, 0.2 mmol), and triphenylphosphine (53 mg, 0.2 mmol). The reaction was stirred at room temperature overnight. The reaction was quenched with water (20 mL) and extracted into ethyl acetate (3×25 mL). The combined organic layers were washed with a brine solution (10 mL) and dried over $MgSO_4$. After filtration, rotary evaporation afforded a brown viscous oil. Mass Spectroscopic analysis of the product eluting from the reversed-phase HPLC column at between 13 and 15 minutes confirmed the presence of compound B.

EXAMPLE 7
Infectiveness of *C. albicans* strains lacking the FAS gene

EXAMPLE 7A
Description of the *C. albicans* strains

The following experiments show that the gene for FAS is important to the ability of *Candida albicans* to infect. This has been done by "knocking out" or rendering ineffective one or both alleles of the FAS gene of the CA14 strain of *Candida albicans* and comparing the ability of these derivative strains to the parent strain to establish an oral infection in Sprague-Dawley rats and a systemic infection in BALB/c mice. The experiments have shown that the parent strain and strains having one residual FAS allele remain able to establish an infection, while a strain in which both alleles have been knocked out is ineffective in producing an infection.

Specifically, to test whether the FAS is necessary to fungal infection, a number of *C. albicans* strains were developed. These had the following characteristics:

| Strain | Characteristics |
|---|---|
| SC5214 | The parent to the strains described below. Described in Fonzi and Irwin, Genetics 134: 717–728, 1993. This strain is virulent. Cole et al., FEMS Microbiol. Letts. 126: 177–180, 1995; Meitner et al., Infect. Immuno. 58: 228–2236, 1990. |
| CA14 | A URA3 double mutant. Described in Fonzi and Irwin, Genetics 134: 717–728, 1993. |
| CFD1 | A derivative of CA14 that is Ura$^+$ where a single FAS2 allele has been disrupted. The strain expresses 80% of the FAS activity of CA14. |
| CFD2 | A derivative of CA14 that is Ura$^+$ where one FAS2 allele has been deleted and the other disrupted. The strain expresses no detectable FAS. |
| CFD3 | A derivative of CFD2 where one FAS2 allele has been restored. The strain expresses 80% of the FAS activity of CA14. |

The methods used to make these derivative strains are described in Fonzi and Irwin, cited above. FAS2 sequences used were selected from the sequences identified in Southard and Cihlar, *Gene* 156: 133–138 and correspond to the condensation reaction domain.

EXAMPLE 7B
Systemic candidiasis

The requirement for FAS for virulence was tested in the murine model developed by Bulaw et al., *Proc. Natl. Acad. Sci. USA* 92: 10570–10574, 1995. BALB/c mice were divided into experimental groups of 10. Each animal in a group was inoculated via the lateral tail vein with a given strain at a given inoculum size. Morbidity and mortality were observed for a three week period. Animals exhibiting severe morbidity were sacrificed immediately.

At eleven days post-inoculation, all animals infected with $10^6$ cfu of SC5314, CFD1 and CFD3 were dead. All animals infected with $10^7$ cfu (10-times $LD_{100}$ of CFD2 were healthy after eleven days. The results indicated that fungal cells lacking FAS were unable to establish a systemic infection.

EXAMPLE 8
Isolation of Patulodin

A 12 liter fermentation of CK2108 was extracted as described in Example 1. The material that was insoluble in the CPC solvent of Example 1 was isolated by vacuum filtration and chromatographed by silica gel flash column chromatography eluted with increasing concentrations of ethyl acetate in hexane. One fraction isolated by this technique was determined by NMR to be patulodin.

EXAMPLE 9
Sephadex LH-20 purification of Compound B

Extract material that was soluble in the CPC solvent was dried, redissolved in methanol and chromatographed on Sephadex LH-20 (Pharmacia, Uppsala, Sweden) using methanol as the eluent. The major peak from this fractionation was dried, redissolved in the two-phase mixture of CPC solvents, and subjected to the CPC chromatography described in Example 1.

EXAMPLE 10
FAS Inhibition by Compound B

*C. Albicans* strain 4918 (available from Dr. Ronald Cihlar, Georgetown University Medical Center, Washington, D.C.) was grown in minimal medium (M63 media available from Difco, Detroit, Mich.) at 37° C. to mid-log phase. 10 $\mu$g/ml cerulenin and 25 $\mu$g/ml of compound B were added to separate cultures. At 15 minute intervals, 20 ml samples were removed and extracts prepared by mechanical extraction as in Example 1C, except that the ammonium sulfate precipitation step was not applied. The extract was diluted to 1 ml to form a solution containing 0.4M potassium phosphate, pH 7.3, 0.125 $\mu$M dithiothreitol, 50 $\mu$M acetyl-CoA, 100 $\mu$M NADPH. After incubation at 37° C. for 5 minutes, 100 $\mu$M malonyl-CoA containing 0.5 $\mu$Ci [2-$^{14}$C]- malonyl-CoA (Amersham, Arlington Heights, Ill.). After 10 minutes at 37° C., the fatty acid synthesis reaction was terminated by adding 30 μl of 60% perchloric acid (v/v) and 1 ml ethanol. Four volumes of pet. ether were added to each reaction incubation to extract the fatty acids. The relative incorporation of malonyl-CoA into fatty acids was determined by liquid scintillation counting. The results were as follows:

| Time of Treatment | Percent Remaining FAS Activity | |
|---|---|---|
| (minutes) | Cerulenin | Compound B |
| 15 | 20 | 53 |
| 30 | 12 | 40 |
| 45 | N.D. | 35 |
| 60 | N.D. | 22 |

We claim:

1. A method of treating or preventing a microbial infection comprising administering to a plant having a composition comprising an infection treating effective amount of a compound of formula I:

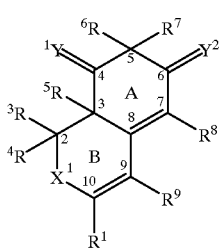

or a pharmaceutically acceptable salt thereof,
wherein
(1) $Y^1$ and $Y^1$ are independently O or S;
(2) $R^1$
  (i) is a straight-chained aliphatic group having about 2 to about 12 carbon atoms,
  (ii) the aliphatic group which additionally comprises an about 3 to about 8-membered carbocyclic ring consisting of three or more additional carbon atoms, or
  (iii) the aliphatic group which additionally comprises an about 3 to about 8-membered heterocyclic ring, wherein the heterocyclic ring contains up to 4 nitrogen atoms, up to 2 sulfur atoms, up to 2 oxygen atoms or additional carbon atoms,
(2a) wherein the carbocyclic or heterocyclic ring atoms can have 1 to 4 substituents chosen from one or more of the following groups fluoro, chloro, bromo, iodo, hydroxy, (C1–C6) alkoxy, (C1–C6) alkyl, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C3) haloalkyl, which can be fully or partially halogenated wherein halo is fluoro, chloro, bromo or iodo, and alkanoylalkyl wherein alkanoyl is C2–C6 and alkyl is C1–C6;

(2b) wherein the non-ring portions of the straight-chained aliphatic group can be substituted with up to 4 of a (C1–C6) aliphatic group, fluoro, chloro, bromo, iodo, hydroxy, (C1–C6) alkoxy, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C6) alkyl, (C1–C3) haloalkyl, which can be fully or partially halogenated wherein halo is fluoro, chloro, bromo or iodo, or alkanoylalkyl wherein alkanoyl is C2–C6 and alkyl is C1–C6;

(3) X is oxygen;

(4) $R^2$ is hydroxy, amino which can be substituted with one or two (C1–C8) alkyl groups, (C1–C8) alkyl, (C7–C10) arylalkyl, (C1–C8) alkoxy, (C1–C8) alkanoylamino or aminocarbonyl which can be N-substituted with one or two (C1–C8) alkyl groups, wherein $R^2$ can be substituted with up to 4 of alkylcarbonyloxy wherein alkyl can be C1–C6, alkoxycarbonyl wherein alkoxy can be C1–C6, hydroxycarbonyl, fluoro, chloro, bromo, iodo, hydroxy, (C1–C3) alkoxy, amino which can be substituted with one or two (C1–C6) alkyl groups, nitro, aminocarbonyl which can be N-substituted with one or two (C1–C6) alkyl groups, cyano, (C1–C3) alkylsulfonamido, (C1–C8) alkanoylamino, (C1–C3) haloalkylsufonamido, (C1–C3) alkyl, (C1–C3) haloalkyl, or alkanoylalkyl wherein alkanoyl is C2–C3 and alkyl is C1–C3;

(5) $R^3$ and $R^5$ either (a) each represent a half bond that together forms a double bond, or (b) $R^3$ is hydrogen and $R^5$ is hydrogen, aliphatic group having 1 to 3 carbons, fluoro, chloro, bromo, iodo, nitro, cyano, hydrocarbonyl, alkylcarbonyloxy wherein alkyl can be C1–C6, alkoxycarbonyl wherein alkoxy can be C1–C6, hydroxycarbonyl, (C1–C8) alkoxy, (C1–C8) alkanoylamino, (C1–C5) alkylsulfonamido, hydroxy, amino which can be substituted with one or two (C1–C3) alkyl groups, aminocarbonyl that can be N-substituted with one or two (C1–C6) alkyl groups, (C1–C3) haloalkylsulfonamido, (C1–C3) haloalkyl, or alkanoylalkyl wherein alkanoyl is C2–C3 and alkyl is C1–C3;

(6) $R^4$ is an aliphatic group having 1 to 3 carbons, cyano, hydroxycarbonyl, alkylcarbonyloxy wherein alkyl can be C1–C6, or alkoxycarbonyl wherein alkoxy can be C1–C6;

(7) $R^8$ and $R^9$ are independently hydrogen, aliphatic group having 1 to 3 carbons, fluoro, chloro, bromo, iodo, nitro, cyano, carboxyaldhyde, hydroxycarbonyl, alkylcarbonyloxy wherein alkyl can be C1–C6, alkoxycarbonyl wherein alkoxy can be C1–C6, (C1–C8) alkoxy, (C1–C8) alkanoylamino or (C1–C5) alkylsulfonamido;

(8) $R^6$ is a (C1–C6) aliphatic group, (C6–C10) aryl, (C7–C10) aralkyl, or a (C1–C3) aliphatic group substituted with a 5 or 6-membered heteroaromatic ring having up to 4 heteroatoms comprising nitrogen, sulfur or oxygen atoms; and (9) $R^7$ is —O—$R^{10}$ or —O—(C=O)—$R^{11}$ where $R^{10}$ is a hydrogen or $R^{10}$ and $R^{11}$ are (9a) an aliphatic group with 1 to 6 carbons, which aliphatic group may be substituted with one to 3 of: hydroxy, fluoro, chloro, bromo, iodo, cyano, amino which can be substituted with one or two (C1–C3) alkyl groups, (C1–C6) alkanoylamino, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, (C1–C5) alkylsulfonate which can be partially or fully halogenated wherein halo is fluoro, chloro, bromo or iodo, (C1–C3) alkoxy, nitro, (C1–C6) alkyl, (C1–C3) haloalkyl, alkanoylalkyl wherein alkanoyl is C2–C3 and alkyl is C1–C3, or hydrocarbonyl, and wherein the aliphatic group can be substituted with an aryl or heteroaryl group where the aryl or heteroaryl moiety comprises a 6 or 10-membered aromatic ring, of which up to 4 ring atoms can be nitrogen heteroatoms, (9a1) wherein the aryl or heteroaryl group can be substituted with up to 4 substituents selected from the group consisting of (C1–C3) aliphatic group, fluoro, chloro, nitro, cyano, carboxyaldhyde, carboxyl, alkylcarbonyloxy wherein alkyl can be C1–C6, alkoxycarbonyl wherein alkoxy can be C1–C6, aminocarbonyl which can be substituted with one or two (C1–C6) alkyl groups, amino, amino substituted with one or two (C1–C3) hydrocarbons, (C1–C6) alkanoylamino, hydroxy, (C1–C3) alkoxy, amino, (C1–C3) alkylsulfonate, (C1–C3) haloalkylsufonate, (C1–C3) haloalkyl, and alkanoylalkyl wherein alkanoyl is C2–C6 and alkyl is C1–C6 or (9b) an aryl or heteroaryl group where the aryl or heteroaryl group comprises a 6 or 10-membered aromatic ring, of which up to 4 ring atoms can be nitrogen, wherein the aryl or heteroaryl group can be substituted with up to 4 substituents selected from the group consisting of (C1–C3) alkyl, (C1–C3) alkenyl, fluoro, chloro, iodo, bromo, nitro, cyano, carboxyaldhyde, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, amino, amino substituted with one or two (C1–C3) aliphatic groups, (C1–C6) alkanoylamino, carboxyl (C1–C6) ester, hydroxy, (C1–C3) alkoxy, (C1–C3) alkylsulfonamido, (C1–C3) haloalkylsulfonamido, (C1–C3) haloalkyl, or alkanoylalkyl wherein alkanoyl is C2–C3 and alkyl is C1–C3, wherein the following proviso applies: when $R^7$ is acetyl the compound differs from chrysodin by at least one of (a) the presence or absence of a methylene, (b) the presence of sulfur in the compound in place of an oxygen, (c) the presence of halo, hydroxy, alkoxy, amino, nitro, alkanoylamino, aminocarbonyl, substituted aminocarbonyl, alkoxycarbonyl, hydroxycarbonyl, cyano, alkylsulfonamido, haloalkylsulfonamido, mono or di-alkylamino, alkanoylalkyl or hydrocarbonyl or (d) the presence in $R^1$ or $R^7$ of a carbocyclic or heterocyclic ring.

2. The method of claim 1, wherein the microbial infection is a fungal infection.

3. The method of claim 2, wherein the fungal infection is caused by a fungus selected from the group consisting of fungi of the genus Oomycetes, Trichoderma, Alternaria, Fusarium, Ascobolus, Phoma, Rhizoctonia, Pythium, Cladosporium, Truncatella, Septoria, Helminthosporium, Aspergillus, Botrytis, Rhizopus and Nectria.

4. The method of claim 1 wherein the organism is infected or at risk of infection with a microbe that expresses fatty acid synthetase, the composition comprising an amount of a compound of formula I effective to inhibit said expressed fatty acid synthetase.

5. The method of claim 1, wherein the heterocyclic ring of $R^1$ is a heteroaryl moiety.

6. The method of claim 5, wherein the heteroaryl moiety of $R^1$ or $R^7$ is a pyridyl, thienyl, furanyl, pyrazinyl, pyrrolyl, indolyl, pyrimidyl, thiazolyl, isothiazolyl, oxazolyl, isoxazolyl, triazolyl, tetrazolyl, quinolyl or isoquinolyl.

7. The method of claim 1, wherein the carbocyclic ring of $R^1$ is a aryl moiety.

8. The method of claim 7, wherein the aryl moiety of $R^1$ or $R^7$ is phenyl or naphthyl.

9. The method of claim 1, wherein $R^7$ includes at least one hydroxy.

10. The method of claim 1, wherein the aliphatic group of $R^1$ has from about 2 to about 6 carbons.

11. The method of claim 1, wherein the halo substituents are fluoro.

12. The method of claim 1, wherein the compound is according to formula II:

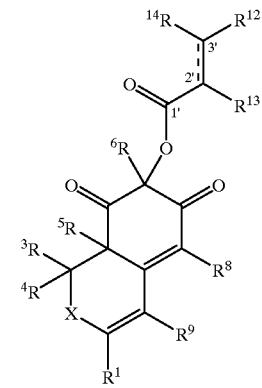

II wherein the bond indicated by the parallel solid and broken lines can be a single or double bond where, if a double bond, it can be a cis or trans double bond, wherein $R^{12}$ is aminocarbonyl which can be substituted with one or two (C1–C6) alkyl groups, hydroxycarbonyl, alkoxycarbonyl wherein alkoxy can be C1–C6, alkylcarbonyloxy wherein alkyl can be C1–C6, or trifluoromethanesulfate, $R^{13}$ is hydrogen or C1 to C3 alkyl, and $R^{14}$ is hydrogen, C1 to C3 alkyl, or hydroxy.

13. A method of treating a fungal infection of claim 1, wherein $R^1$ conforms to one of the following formulas:

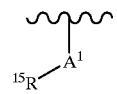

III

-continued

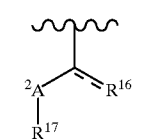

IV

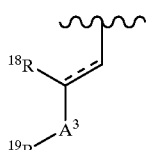

V

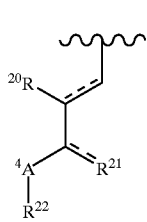

VI

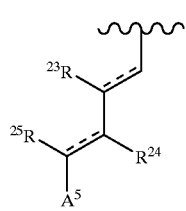

VII wherein the bonds represented with dashed lines are single or double bonds, $R^{15}$, $R^{17}$, $R^{19}$ and $R^{22}$ are (C1–C10) aliphatic groups, $R^{16}$, $R^{18}$, $R^{20}$, $R^{21}$, $R^{23}$, $R^{24}$ and $R^{25}$ are methyl, methylene or hydrogen, wherein $A^1$, $A^2$, $A^3$, $A^4$ and $A^5$ are six-membered aromatic or heterocyclic rings, having up to 4 nitrogen ring atoms and the rest carbon, $A^1$, $A^2$, $A^3$, $A^4$ and $A^5$ can be substituted with up to 4 substituents selected from the group consisting of fluoro, chloro, bromo, iodo, nitro, cyano, amino, (C1–C3) mono or di-alkylamino, (C1–C8) alkanoylamino, (C1–C3) alkylsulfonamido, (C1–C3) haloalkylsulfonamido which can be fully or partially halogenated wherein halo is fluoro, chloro, bromo or iodo, aminocarbonyl which can be substituted with one or two (C1–C6) alkyl groups, alkylcarbonyloxy wherein alkyl can be C1–C6, (C1–C6) alkoxycarbonyl, hydroxycarbonyl, (C1–C3) haloalkyl, which can be fully or partially halogenated wherein halo is fluoro, chloro, bromo or iodo, hydroxy, (C1–C8) alkoxy, and alkanoylalkyl wherein alkanoyl can be C2–C3 and alkyl can be C1–C3, and wherein the dashed lines indicate bonds that are either double or single bonds.

14. The method of claim 13, wherein $R^{15}$, $R^{17}$, $R^{19}$ and $R^{22}$ include an unsaturated bond conjugated to another unsaturated bond.

15. The method of claim 13, wherein the illustrated two bonds linking $A^1$, $A^2$, $A^3$, and $A^4$ are meta to each other.

16. The method of claim 13, wherein at least one of the dashed lines in each of formulas III–VII represents a double bond.

17. The method of claim 1, wherein $R^3$ and $R^5$ each represent a half bond that together forms a double bond, or $R^3$ is hydrogen and $R^5$ is hydrogen.

18. The method of claim 1, wherein the following applies:
(I) when $R^7$ is 2,4-dihydroxypentyl the compound of the invention differs from patulodin by at least one of (2a) the presence or absence of a methylene, (2b) the presence of sulfur in the compound in place of an oxygen, (2c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde, (2d) the presence in $R^1$ or $R^7$ of a carbocyclic or heterocyclic ring or (2e) the absence of an epoxide moiety;

(II) either the 7-position of the A ring is not substituted with chloro or the $R^1$ position differs from a 3,5-dimethyl-hepta-1,3-dienyl group; and (III) $R^7$ is either (a) not one of 2-methyl-3,5-dihydroxyphenylcarbonyl or methyl or (b) $R^1$ is not one of propyl-2-enyl, 1-hydroxypropyl-2-enyl or 1-carboxylethylenyl.

19. A method of treating or preventing a microbial infection comprising administering to a plant having a composition comprising an infection treating effective amount of a compound of formula I:

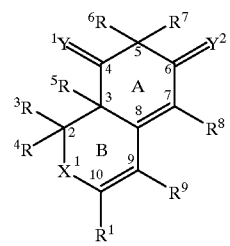

I or a pharmaceutically acceptable salt thereof,
wherein
(1) $Y^1$ and $Y^1$ are independently O or S;
(2) $R^1$
 (i) is a straight-chained aliphatic group having about 2 to about 12 carbon atoms,
 (ii) the aliphatic group which additionally comprises an about 3 to about 8-membered carbocyclic ring consisting of three or more additional carbon atoms, or
 (iii) the aliphatic group which additionally comprises an about 3 to about 8-membered heterocyclic ring, wherein the heterocyclic ring contains up to 4 nitrogen atoms, up to 2 sulfur atoms, up to 2 oxygen atoms or additional carbon atoms, (2a) wherein the carbocyclic or heterocyclic ring atoms can have 1 to 4 substituents chosen from one or more of the following groups fluoro, chloro, bromo, iodo, hydroxy, (C1–C6) alkoxy, (C1–C6) alkyl, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C3) haloalkyl, which can be fully or partially halogenated wherein halo is fluoro, chloro, bromo or iodo, and alkanoylalkyl wherein alkanoyl is C2–C6 and alkyl is C1–C6;

(2b) wherein the non-ring portions of the straight-chained aliphatic group can be substituted with up to 4 of a (C1–C6) aliphatic group, fluoro, chloro, bromo, iodo, hydroxy, (C1–C6) alkoxy, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C6) alkyl, (C1–C3) haloalkyl, which can be fully or partially halogenated wherein halo is fluoro, chloro, bromo or iodo, or alkanoylalkyl wherein alkanoyl is C2–C6 and alkyl is C1–C6;

(3) X is oxygen;

(4) $R^2$ is hydroxy, amino which can be substituted with one or two (C1–C8) alkyl groups, (C1–C8) alkyl, (C7–C10) arylalkyl, (C1–C8) alkoxy, (C1–C8) alkanoylamino or aminocarbonyl which can be N-substituted with one or two (C1–C8) alkyl groups, wherein $R^2$ can be substituted with up to 4 of alkylcarbonyloxy wherein alkyl can be C1–C6, alkoxycarbonyl wherein alkoxy can be C1–C6, hydroxycarbonyl, fluoro, chloro, bromo, iodo, hydroxy, (C1–C3) alkoxy, amino which can be substituted with one or two (C1–C6) alkyl groups, nitro, aminocarbonyl which can be N-substituted with one or two (C1–C6) alkyl groups, cyano, (C1–C3) alkylsulfonamido, (C1–C8) alkanoylamino, (C1–C3) haloalkylsufonamido, (C1–C3) alkyl, (C1–C3) haloalkyl, or alkanoylalkyl wherein alkanoyl is C2–C3 and alkyl is C1–C3;

(5) $R^3$ and $R^5$ either (a) represent a common oxygen forming an epoxide, (b) each represent a half bond that together forms a double bond, or (c) $R^3$ is hydrogen and $R^5$ is hydrogen, aliphatic group having 1 to 3 carbons, fluoro, chloro, bromo, iodo, nitro, cyano, hydrocarbonyl, alkylcarbonyloxy wherein alkyl can be C1–C6, alkoxycarbonyl wherein alkoxy can be C1–C6, hydroxycarbonyl, (C1–C8) alkoxy, (C1–C8) alkanoylamino, (C1–C5) alkylsulfonamido, hydroxy, amino which can be substituted with one or two (C1–C3) alkyl groups, aminocarbonyl that can be N-substituted with one or two (C1–C6) alkyl groups, (C1–C3) haloalkylsulfonamido, (C1–C3) haloalkyl, or alkanoylalkyl wherein alkanoyl is C2–C3 and alkyl is C1–C3;

(6) $R^4$ is an aliphatic group having 1 to 3 carbons, cyano, hydroxycarbonyl, alkylcarbonyloxy wherein alkyl can be C1–C6, or alkoxycarbonyl wherein alkoxy can be C1–C6;

(7) $R^8$ and $R^9$ are independently hydrogen, aliphatic group having 1 to 3 carbons, fluoro, chloro, bromo, iodo, nitro, cyano, carboxyaldhyde, hydroxycarbonyl, alkylcarbonyloxy wherein alkyl can be C1–C6, alkoxycarbonyl wherein alkoxy can be C1–C6, (C1–C8) alkoxy, (C1–C8) alkanoylamino or (C1–C5) alkylsulfonamido;

(8) $R^6$ is a (C1–C6) aliphatic group, (C6–C10) aryl, (C7–C10) aralkyl, or a (C1–C3) aliphatic group substituted with a 5 or 6-membered heteroaromatic ring having up to 4 heteroatoms comprising nitrogen, sulfur or oxygen atoms; and (9) $R^7$ is —O—$R^{10}$ or —O—(C═O)—$R^{11}$ where $R^{10}$ is a hydrogen or $R^{10}$ and $R^{11}$ are (9a) an aliphatic group with 1 to 3 carbons, which aliphatic group may be substituted with one to 3 of: hydroxy, fluoro, chloro, bromo, iodo, cyano, amino which can be substituted with one or two (C1–C3) alkyl groups, (C1–C6) alkanoylamino, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, (C1–C5) alkylsulfonate which can be partially or fully halogenated wherein halo is fluoro, chloro, bromo or iodo, (C1–C3) alkoxy, nitro, (C1–C6) alkyl, (C1–C3) haloalkyl, alkanoylalkyl wherein alkanoyl is C2–C3 and alkyl is C1–C3, or hydrocarbonyl, and wherein the aliphatic group can be substituted with an aryl or heteroaryl group where the aryl or heteroaryl moiety comprises a 6 or 10-membered aromatic ring, of which up to 4 ring atoms can be nitrogen heteroatoms, (9a1) wherein the aryl or heteroaryl group can be substituted with up to 4 substituents selected from the group consisting of (C1–C3) aliphatic group, fluoro, chloro, nitro, cyano, carboxyaldhyde, carboxyl, alkylcarbonyloxy wherein alkyl can be C1–C6, alkoxycarbonyl wherein alkoxy can be C1–C6, aminocarbonyl which can be substituted with one or two (C1–C6) alkyl groups, amino, amino substituted with one or two (C1–C3) hydrocarbons, (C1–C6) alkanoylamino, hydroxy, (C1–C3) alkoxy, amino, (C1–C3) alkylsulfonate, (C1–C3) haloalkylsufonate, (C1–C3) haloalkyl, and alkanoylalkyl wherein alkanoyl is C2–C6 and alkyl is C1–C6 or (9b) an aryl or heteroaryl group where the aryl or heteroaryl group comprises a 6 or 10-membered aromatic ring, of which up to 4 ring atoms can be nitrogen, wherein the aryl or heteroaryl group can be substituted with up to 4 substituents selected from the group consisting of (C1–C3) alkyl, (C1–C3) alkenyl, fluoro, chloro, iodo, bromo, nitro, cyano, carboxyaldhyde, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, amino, amino substituted with one or two (C1–C3) aliphatic groups, (C1–C6) alkanoylamino, carboxyl (C1–C6) ester, hydroxy, (C1–C3) alkoxy, (C1–C3) alkylsulfonamido, (C1–C3) haloalkylsulfonamido, (C1–C3) haloalkyl, or alkanoylalkyl wherein alkanoyl is C2–C3 and alkyl is C1–C3, wherein the following proviso applies: when $R^7$ is acetyl the compound differs from chrysodin by at least one of (a) the presence or absence of a methylene, (b) the presence of sulfur in the compound in place of an oxygen, (c) the presence of halo, hydroxy, alkoxy, amino, nitro, alkanoylamino, aminocarbonyl, substituted aminocarbonyl, alkoxycarbonyl, hydroxycarbonyl, cyano, alkylsulfonamido, haloalkylsulfonamido, mono or di-alkylamino, alkanoylalkyl or hydrocarbonyl or (d) the presence in $R^1$ or $R^7$ of a carbocyclic or heterocyclic ring.

* * * * *